(12) United States Patent
Raffer

(10) Patent No.: US 6,167,752 B1
(45) Date of Patent: Jan. 2, 2001

(54) ROTARY VISCOMETER WITH AN AIR BEARING

(75) Inventor: Gerhard Raffer, Graz (AT)

(73) Assignee: Anton Paar GmbH, Graz (AT)

( * ) Notice: Under 35 U.S.C. 154(b), the term of this patent shall be extended for 0 days.

(21) Appl. No.: 09/180,131

(22) PCT Filed: Apr. 23, 1997

(86) PCT No.: PCT/AT97/00077
§ 371 Date: Aug. 31, 1999
§ 102(e) Date: Aug. 31, 1999

(87) PCT Pub. No.: WO97/42482
PCT Pub. Date: Nov. 13, 1997

(30) Foreign Application Priority Data

May 2, 1996 (AT) ...................................................... 785/96

(51) Int. Cl.[7] .................................................. G01N 11/14
(52) U.S. Cl. ............................................. 73/54.28; 73/843
(58) Field of Search ............................. 73/54.06, 54.28, 73/841, 843, 829, 822, 824

(56) References Cited

U.S. PATENT DOCUMENTS

| 3,886,789 | * | 6/1975 | Brookfield | ........................... 73/54.35 |
| 4,176,002 | * | 11/1979 | Quenisset et al. | ...................... 117/15 |
| 5,905,606 | * | 5/1999 | Johnson et al. | ....................... 360/105 |

* cited by examiner

*Primary Examiner*—Max Noori
(74) *Attorney, Agent, or Firm*—Townsend and Townsend and Crew LLP

(57) ABSTRACT

A rotary viscometer has a measuring motor which drives a measuring shaft that carries a disc mounted in an air bearing of a stator. The viscometer has a normal force measuring drive defined by at least one position sensor for determinal movements of the measuring shaft on the basis of viscoelastic properties of the substance to be investigated, such as a liquid. To measure the normal force in the region of the air bearing, the position sensors are disposed in the region of the air bearing on the stator, and in particular they are embedded in the stator and absorb the movements of the disc in the axial direction of the measuring shaft with resect to the stator.

16 Claims, 3 Drawing Sheets

ROTARY VISCOMETER WITH AN AIR BEARING

BACKGROUND OF THE INVENTION

The invention relates to a rotating viscometer with a measuring motor which drives a measuring shaft which carries a disc mounted in an air bearing of a stator, and with a normal force measuring device having at least one position sensor to determine axial movements of the measuring shaft on the basis of viscoelastic properties of the substance to be investigated, more particularly fluid. The substance to be investigated may be of any kind and should exhibit plastic-elastic behavior, like, for example, rubber, honey, solutions, emulsions, oils, plastics etc.

A rotating viscometer of the type specified in the introduction is known from German patent publication DE 27 33 099 B1, for example. This publication describes a rotating viscometer on the plate-cone or plate-plate principle with two contra-rotating measuring surfaces, with a device for measuring the tempering chamber surrounding the lower measuring surface, wherein the device for measuring the normal force is located in its own housing separate from the measuring surfaces, which, in relation to the machine frame or the tempering chamber, may be located underneath the same by means of a releasable connection. In this arrangement, the normal force on the lower measuring plate is ascertained via the deflection of a bar. This rotating viscometer is complex in construction and the measured values obtained relating to the applied normal force are influenced by a plurality of equipment parameters.

SUMMARY OF THE INVENTION

It is an object of the invention to provide a rotating viscometer, with which the temperature influences for determining the normal force may be determined with a sufficiently high degree of accuracy required by rheologists. Moreover, the rotating viscometer should be capable of being produced simply and so as to be operationally reliable and should allow the highest degree of measurement accuracy. When investigations of solids are performed, they are advantageously preloaded axially with a normal force.

These objects are achieved according to the invention with a rotating viscometer of the type specified in the introduction in that, in order to measure the normal force in the vicinity of the air bearing, the position sensor(s) is (are) arranged in the vicinity of the air bearing on the stator, more particularly embedded in the stator, and absorb the movements of the disc relative to the stator occurring in the axial direction of the measuring shaft. With the rotating viscometer according to the invention, the normal force may be measured without force and without contact, more particularly without friction, without the structure becoming complicated or the measurement accuracy or the operational reliability being adversely affected.

In a constructionally simple embodiment of a rotating viscometer if the features of possible position sensors are, in particular, capacitive, inductive and/or optical (interferometric) position sensors which do not cause any forces in the axial direction of the measuring shaft and cause no friction between the stator and the bearing disc, i.e. force-free and non-contact position sensors.

Very accurate measured values relating to the spacing or the changes of this spacing are obtained which may be evaluated extremely satisfactorily to determine the normal force.

Advantageous embodiments of rotating viscometers of the invention have position sensors acting without force and without contact formed at advantageous locations.

DESCRIPTION OF THE PREFERRED EMBODIMENTS

Figure 1:
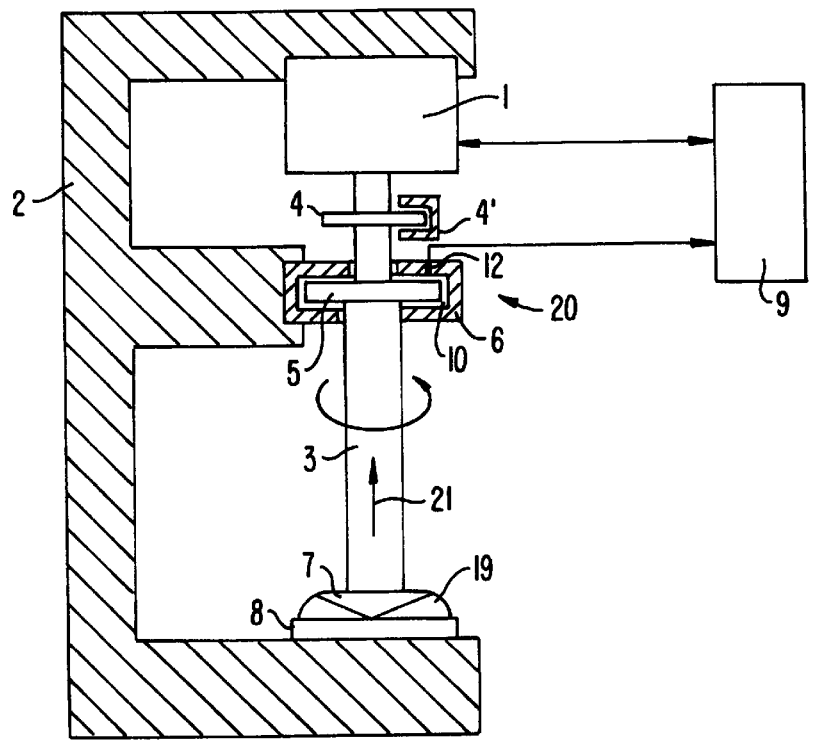
FIG. 1 shows the structure of a rotary viscometer according to the invention.

FIG. 1 shows in schematic form the structure of a rotating viscometer according to the invention. Conventional rotating viscometers also essentially exhibit a structure of this kind, but with the exception that the measuring sensor 12 provided or the several measuring sensors provided are not—as provided according to the invention—arranged in the vicinity of the air bearing but, being arranged at another location, monitor an axial movement of the measuring shaft 3.

The rotating viscometer represented in FIG. 1 comprises a stand or frame 2 on which is arranged a plate 8 on which the substance 19 to be investigated is placed. A measuring shaft 3 driven by a measuring motor 1 carries, as measuring body, a device for holding solids in place having a construction known per se or a cone 7 or a plate replacing the cone 7, which is rotated by the measuring motor 1 via the measuring shaft 3. With respect to the measuring motor 1, the relationship between the torque on the measuring shaft 3 and the power consumption of the measuring motor 1 is known or is obtained as accurately as possible by means of appropriate calibration measurements. The moment exerted on the measuring shaft by the substance 19 to be investigated via the cone 7 or the plate may consequently be determined by measuring the power consumption of the measuring motor 1.

An angle encoder 4, 4' is arranged on the measuring shaft 3 to enable the rotational position and the rotational speed of the measuring shaft 3 to be ascertained. The measuring motor 1 is mounted in the stator or housing or support 2 so as to be fixed in relation to the plate 8; in addition, the position of the measuring shaft 3 must be determined or fixed, for which purpose a guide bearing for the measuring shaft 3 is formed on the stand 2. This guide bearing is an air bearing 20, in order to meet the measurement requirements imposed on rotating viscometers of this kind. Rotating viscometers are able to resolve substance moments of <0.1 mNm. Conventional roller bearings are not suitable for this application due to excessive roller friction. The use of air bearings solves this problem, as these bearings have low residual friction amounting to ~1 mNm.

There are fundamentally three ways of carrying out investigations:

a) CSR (controlled shear rate) test: in this test the measuring shaft 3 is acted upon with constant rotational speed and the torque is measured and evaluated.

b) CSS (controlled shear stress) test: in this case a constant torque is exerted on the measuring shaft 3 and the rotational speed is measured.

c) Oscillation test: in this test the measuring shaft 3 is acted upon with a torque or rotational movement having a sinusoidal shape, for example, so that, as well as the viscous component, the elastic components of the investigated substance can also be determined.

In a rotational test, Newtonian fluids or ideal fluids exhibit only anti-torque moments in the rotational plane. By contrast, viscoelastic, more particularly dough- or paste-like or plastic-elastic substances or fluids, additionally generate a force F (FIG. 2), the direction of which is normal to this rotational plane and is indicated in FIG. 1 by the arrow 21. This force is referred to in rheology as "normal force" and provides an important characteristic for the (molecular) structure of the substance 19.

Figure 2:
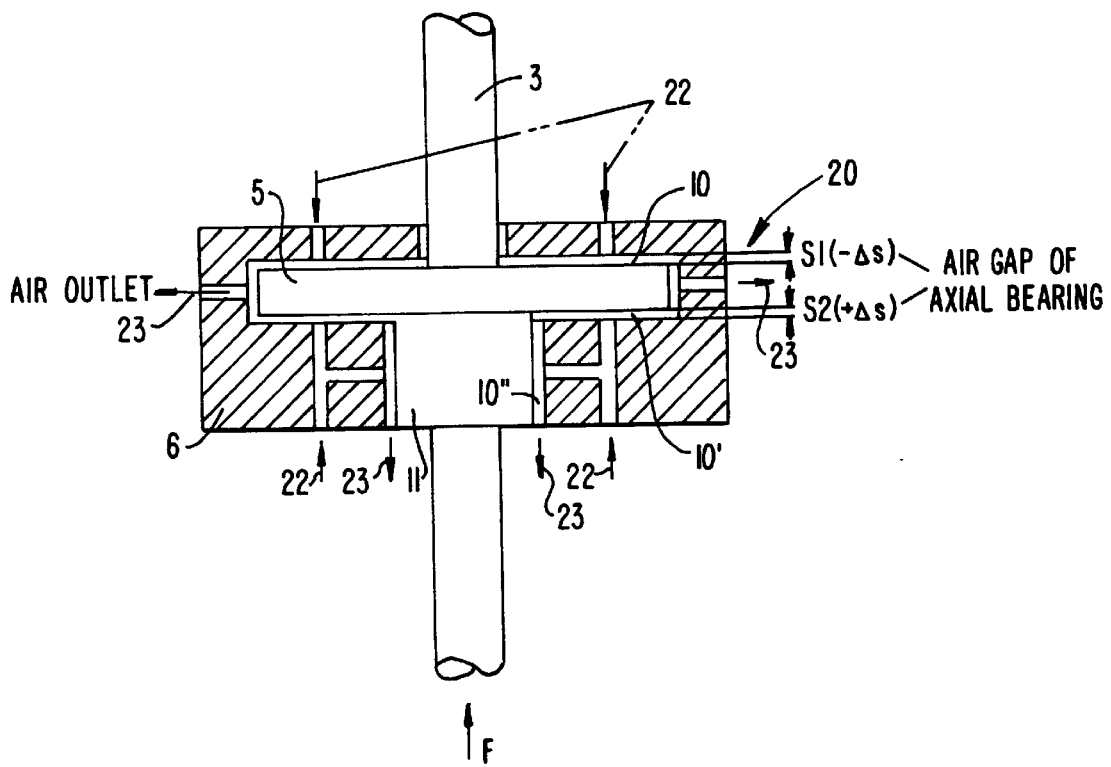
FIG. 2 shows the structure of an air bearing.

The use of air bearings 20, as represented schematically in FIG. 1 and FIG. 2, for rotating viscometers is known per se. Air bearings 20 of this kind essentially comprise a stator 6 fixed to a stand or housing, and a disc or rotor 5 which is mounted so as to be rotatable therein and is fixedly connected to the measuring shaft 3. The disc 5 serves to absorb the axial load acting on the measuring shaft 3, as a result of its weight, for example, and is supported against the stator 6 by way of an air cushion. A cylindrical component 11 attached to the measuring shaft 3 underneath and/or above the disc 5 forms a radial bearing which centers the measuring shaft 3 in the stator 6 by means of the air cushion surrounding the said radial bearing. Air is supplied to the air bearing via air inlets 22 from supply installations which are not represented and this air supplied under pressure supports the disc 5 underneath and above and the component 11 radially. The air supplied escapes via air outlets 23. The air supply takes place under as constant a pressure as possible. The rigidity of the air bearing 20 essentially depends on the air cushion area, the size of the air gaps 10 and 10' and also the pressure in the air gaps 10 and 10'. Under axial loading by the normal force F in the direction of the arrow 21, i.e. corresponding axial loading of the measuring shaft 3, the air cushion of the air gaps 10, 10' counteracts this normal force F in a similar way to a spring. A force acting axially may thus produce an air gap change in the air bearing 20, wherein the movements or displacement changes of the measuring shaft 3 or the changes of the thickness of the air gaps 10, 10' are proportional to the force exerted or are in a mathematical relationship therewith. On the basis of the proportionality or the existing mathematical relationship, conclusions relating to the force exerted may be drawn by measuring the thickness and/or the change of the air gaps 10, 10', i.e. the position or displacement change of the measuring shaft 3 in its axial direction.

To determine this force, normal force measuring devices are associated with rotating viscometers of this kind, wherein the position sensors provided for establishing the position change of the measuring shaft 3 are arranged at any location of the measuring shaft 3, more particularly in the vicinity of the measuring motor 1. Capacitive and/or inductive position sensors of this kind allow non-contact measurement of the displacement of the measuring shaft 3. A substantial disadvantage of these known embodiments, however, lies in the fact that, with changes in temperature, the thermal expansion between the air bearing disc 5 and the installation location of the position sensor produces a distance change, this distance conventionally amounting to a few centimeters, which distance change is certainly not produced by the normal force to be measured. In view of the low force and distance values which are to be measured, a rotating viscometer designed in this way reacts distinctly sensitively to temperature changes. In known rotating viscometers, a high air bearing rigidity is required to keep the measurement gap filled with the substance 19 constant. Conventionally, this is 10 N/mm. In addition, the normal force F is to be measured with a resolution of 10 mN; this corresponds to a resolution in the distance measurement of 1 nm.

Assuming an expansion coefficient of $1\times10^{-5}$ $1/°$ C. of the measuring shaft 3, if this is made of steel, and a distance between the bearing disc 5 and the position sensor of 30 mm, a temperature coefficient of 300 nm/° C. or a drift of the normal force F of 3000 mN/° C. is calculated. Because of the temperature influence, such arrangements are of only limited suitability for determining the normal force F with a degree of accuracy usually required by rheologists.

Figure 3:
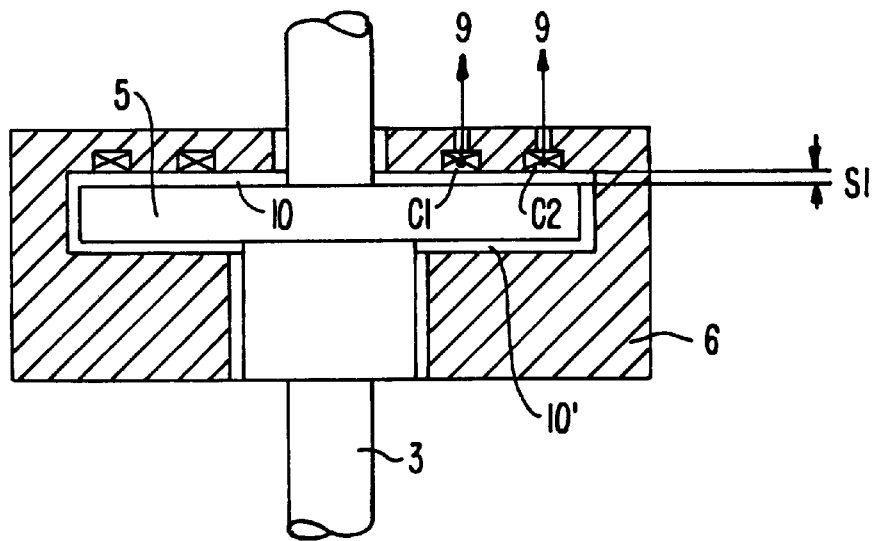
FIGS. 3, 4, 5 and 6 show various embodiments according to the invention of an air bearing with normal force measurement.

In principle, the arrangement of only one single position or spacing sensor is sufficient; better measurement results are obtained by multiple measurements. FIG. 3 now shows an embodiment of a rotating viscometer according to the invention, in which capacitive position sensors are provided which are formed by capacitors $C_1$ and $C_2$ arranged in the stator 6 in the immediate vicinity of the upper air gap 10. With the aid of these capacitive position sensors $C_1$ and $C_2$ or their output signals, the spacing of the bearing disc 5 from these position sensors $C_1$, $C_2$ or a change of this spacing may be determined by means of the normal force measuring device 9. The two position sensors, arranged concentrically and formed in the present case by capacitor rings, form two capacitors with the bearing disc 5. An occurrence of a normal force F causes lifting of the measuring shaft 3 and a reduction in the thickness S1 of the upper air gap 10 by a value _s and an increase in the thickness S2 of the lower air gap 10' by a value _s. The change of the capacitance values of the capacitive measuring sensors may now be measured, evaluated, stored and, if appropriate, indicated as a normal force F with circuits, e.g. bridge circuits, which are known per se.

Instead of the capacitor rings surrounding the measuring shaft 3, capacitor plates may also be used. The capacitor rings have the advantage, however, that the air gap is measured virtually over the whole surface of the bearing disc 5 and consequently mechanical eccentricity of the bearing disc 5 within a rotation does not affect the measurement.

Figure 4:
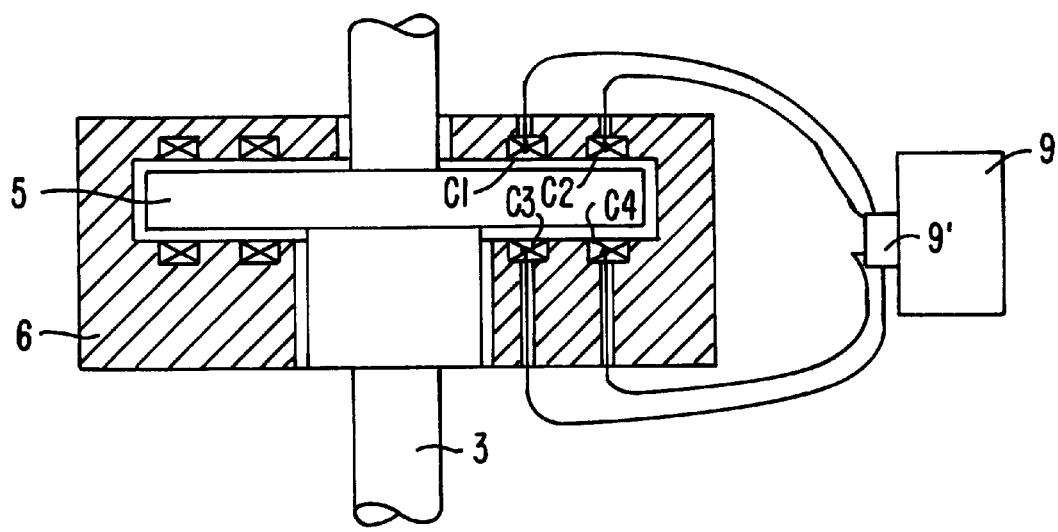

Combined measurement of the thickness S1, S2 of the air gaps 10 and 10' is represented in FIG. 4. The changes of the gap thickness are advantageously measured and the difference is formed from the measured values, thus producing considerable advantages. Thermal expansion of the disc 5 and/or of the stator 6 causes, both in the upper air gap 10 and in the lower air gap 10', a distance change between the respective upper and lower surface of the disc 5 and the respective inside surfaces of the stator 6 directed towards these surfaces. The two air gaps 10, 10' become either greater or smaller. On the basis of the difference-formation of the two measurement signals provided, no normal force change is detected, however, despite the change of thickness of the air gaps. Axial loading of the measuring shaft 3 or the disc 5 at the occurrence of a normal force F, on the other hand, causes a change of thickness of the upper air gap 10 and of the lower air gap 11 [sic, recte 10']:

Upper air gap: S1 (−_s)

Lower air gap: S2 (+_s).

These changes have different signs and, where the values for S1 and S2 are known, a signal value is produced on the basis of the difference-formation as the measurement signal for the change, which signal value corresponds to double the change due to the normal force F which has occurred. Thermal changes of the air gaps 10, 10' are compensated for by the system by simultaneous doubling of the measurement signal and corresponding increase of the resolution.

Figure 5:
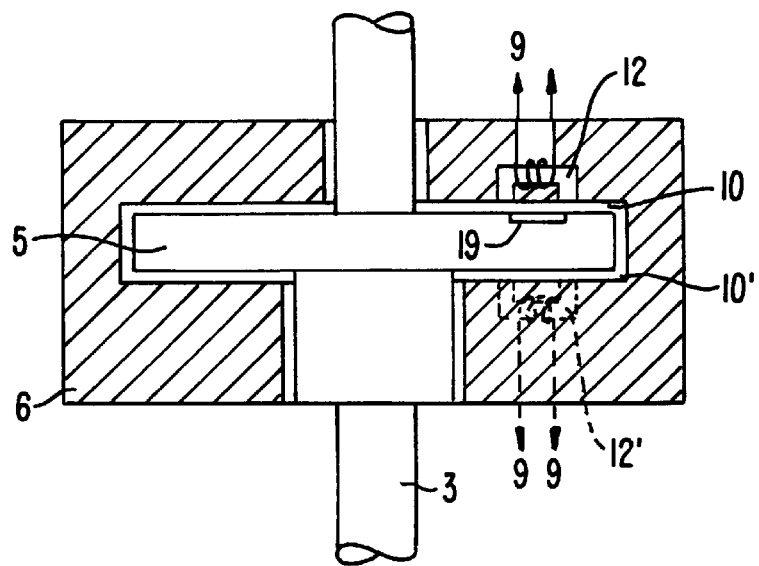

FIG. 5 shows an embodiment of a rotating viscometer according to the invention in which the spacing or distance measurement is effected with at least one inductive position sensor 12. A change of the thickness of the air gap 10 due to lifting or lowering of the disc 5 causes a change of the induction in the magnetic circuit. The change of the induction is in a known mathematical relationship with the change of thickness which has occurred or change of the spacing of the bearing disc 5 from the position sensor 12, from which relationship the normal force F may be determined.

As indicated in FIG. 5 by a broken line, the inductive distance measurement may be performed with two sensors 12, 12' on both sides of the bearing disc 5 and the difference of the signals may be evaluated as described in connection with FIG. 4.

Figure 6:
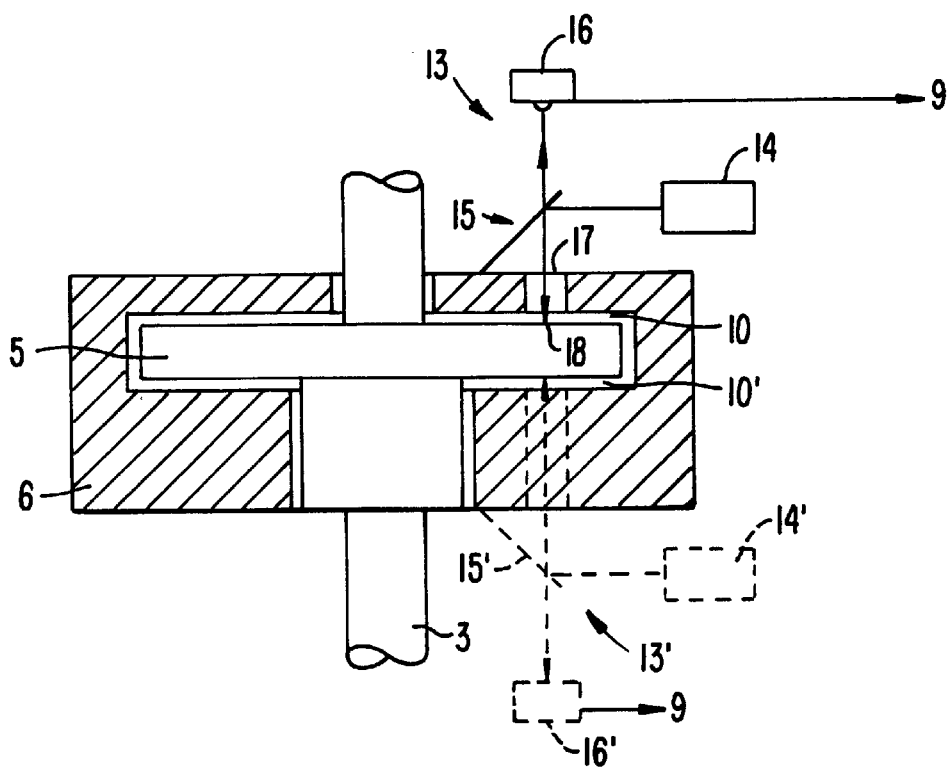

FIG. 6 shows an embodiment of a rotating viscometer according to the invention, in which the thickness of the upper air gap 10 and/or of the lower air gap 10' is monitored with an optical position sensor or an interferometer 13, 13'. Light from the light source 14, 14' is beamed via semi-transparent mirrors 15, 15' onto the surface of the disc 5, reflected there and reflected back by the mirrors 15, 15' onto detectors 16, 16'. The interference images obtained are evaluated as measured values, as described above.

The surfaces located opposite the distance sensors $C_1$, $C_2$, $C_3$, $C_4$, 12, 12', 13, 13' on the bearing disc 5 may be designed so as to cooperate optimally with the position sensors. These surface regions of the bearing disc 5 may be provided with metallic and/or magnetic regions or polished or reflective regions in order to increase the measurement accuracy or sensitivity.

In view of the fact that the position sensors are arranged as close to the bearing disc 5 as possible, all the thermal changes of the measuring shaft 3 in the region between the bearing disc 5 and the position sensors are eliminated. Changes of position of the bearing disc 5 in relation to the position sensors thus always originate from an axial or normal force F exerted on the measuring shaft 3, which force can thus be detected with the greatest accuracy.

It is entirely possible to use combinations of inductive, capacitive or optical position sensors.

What is claimed is:

1. A rotary viscometer comprising a measuring motor which drives a measuring shaft which bears a disc mounted in an air bearing of a stator, a normal force measuring device having at least one position sensor to determine axial movements of the measuring shaft due to viscoelastic properties of a fluid to be investigated, the at least one position sensor being arranged in a vicinity of the air bearing of the stator for measuring a normal force in the vicinity of the air bearing and picking up movements of the disc relative to the stator occurring in the axial direction of the measuring shaft.

2. A rotary viscometer according to claim 1 wherein the at least one position sensor is arranged on the stator at at least one of in or just above an upper end region of an upper air gap of the air bearing and just beneath a lower end region of a lower air gap of the air bearing.

3. A rotary viscometer according to claim 1 wherein at least one of capacitive, inductive and optical position sensors are provided as the at least one position sensor.

4. A rotary viscometer according to claim 1 wherein a spacing of at least one of the upper and/or lower surfaces of the disc from the stator and changes of the spacing are measured with the at least one position sensor, and in that the measurement signals of the at least one position sensor corresponding to the spacing or the chances of the spacing are supplied to the normal force measuring device.

5. A rotary viscometer according to claim 1 wherein at least one position sensor is arranged above and at least one position sensor is arranged below the disc on or in the stator.

6. A rotary viscometer according to claim 5 wherein the position sensors located above and below the disc are respectively connected to a difference-forming element or a unit forming the difference of the signal values and appropriately integrated in the normal force measuring device.

7. A rotary viscometer according to claim 1 including means arranged on the disc and cooperating with a respective one of the at least one position sensor for improving the quality of the measurement signal.

8. A rotary viscometer according to claim 1 wherein the at least one position sensor comprises a capacitive measuring sensor in the form of a capacitor ring surrounding the measuring shaft and formed on the stator.

9. A rotary viscometer according to claim 1 wherein a yoke inserted in a recess of the stator and surrounded with a coil comprises an inductive position sensor.

10. A rotary viscometer according to claim 1 wherein the stator includes a recess for illuminating the disc via a semi-transparent mirror, and including a semi-transparent mirror for passing light reflected by the disc to a detector for interferometric evaluation.

11. A rotary viscometer according to claim 1 wherein the air bearing is recessed in the stator.

12. A rotary viscometer according to claim 3 wherein the at least one position sensor comprises an interferometric position sensor.

13. A rotary viscometer according to claim 7 wherein the means for improving the quality of the measurement signal includes at least one of a metal coating, a magnetic coating, a reflective surface region and a polished surface region.

14. A rotary viscometer according to claim 13 wherein the means for improving the quality of the measurement signal is located opposite at least one position sensor.

15. A rotary viscometer according to claim 9 wherein the yoke is horseshoe-shaped.

16. A rotary viscometer according to claim 10 wherein the semitransparent mirror is connected to the normal force measuring device.

* * * * *